United States Patent [19]

Groman et al.

[11] Patent Number: 5,554,386
[45] Date of Patent: Sep. 10, 1996

[54] DELIVERY OF THERAPEUTIC AGENTS TO RECEPTORS USING POLYSACCHARIDES

[75] Inventors: Ernest V. Groman, Brookline; Edward T. Menz, Quincy; Philip M. Enriquez, Sheldonville; Chu Jung, Arlington; Jerome M. Lewis, Newton; Lee Josephson, Arlington, all of Mass.

[73] Assignee: Advanced Magnetics, Inc., Cambridge, Mass.

[21] Appl. No.: 260,551

[22] Filed: Jun. 16, 1994

Related U.S. Application Data

[63] Continuation-in-part of Ser. No. 900,686, Jun. 17, 1992, Pat. No. 5,478,576, which is a continuation-in-part of Ser. No. 936,873, Aug. 27, 1992, Pat. No. 5,336,506, which is a continuation of Ser. No. 630,017, Dec. 19, 1990, abandoned, which is a continuation-in-part of Ser. No. 679,526, Apr. 2, 1991, Pat. No. 5,141,739, which is a continuation of Ser. No. 384,991, Jul. 2, 1989, abandoned, which is a continuation-in-part of Ser. No. 228,640, Aug. 4, 1988, abandoned, which is a continuation-in-part of Ser. No. 67,586, Jun. 26, 1987, Pat. No. 4,827,945, which is a continuation-in-part of Ser. No. 882,044, Jul. 3, 1986, Pat. No. 4,770,183.

[51] Int. Cl.$^6$ .................... A61K 47/26; A61K 31/56; A61K 31/495; A61K 31/70; A61K 39/395; A61K 33/26; A61K 38/21

[52] U.S. Cl. .................... 424/488; 424/646; 435/178; 514/2; 514/21; 514/54; 514/169; 514/179; 536/55.1

[58] Field of Search .................... 424/493, 646, 424/488; 435/178; 514/54, 2, 21, 169, 179; 530/813; 531/551

[56] References Cited

U.S. PATENT DOCUMENTS

| | | | |
|---|---|---|---|
| 2,649,421 | 8/1953 | Stacey et al. | 260/9 |
| 2,765,244 | 10/1956 | Stacey et al. | 127/36 |
| 4,320,194 | 3/1982 | Bull | 435/7 |
| 4,501,726 | 2/1985 | Schroder et al. | 424/1.1 |

(List continued on next page.)

FOREIGN PATENT DOCUMENTS

| | | |
|---|---|---|
| 0186947 | 7/1986 | European Pat. Off. . |
| 88301602 | 2/1988 | European Pat. Off. . |
| 3200766 | 9/1982 | Germany . |
| 3738069 | 5/1989 | Germany . |
| 60-219202 | 11/1985 | Japan . |
| 60-219201 | 11/1985 | Japan . |
| 1051198 | 2/1988 | Japan . |
| 1285094 | 1/1987 | U.S.S.R. . |
| US92/05091 | of 0000 | WIPO . |
| US89/03352 | 8/1989 | WIPO . |
| 9001295 | 2/1990 | WIPO . |
| 9003190 | 4/1990 | WIPO . |

OTHER PUBLICATIONS

1958 Bouveng, *Acta Chemica Scandinavica* 12:1977–1984.
1960 Whistler, *Advances in Carbohydrate Chemistry* 13:289–329.
1967 Albersheem et al., *Carbohydrate Research* 5:340–345.
1971 Nedelcheva et al., *La Chimica e L'Industria* 53:1018–1021.
1973 Richards et al., *Carbohydrate Research* 27:185–191.
1977 Young et al., *Carbohydrate Research* 59:193–201.
1983 Fincher et al., *Ann. Rev. Plant Physiol.* 34:47–70.

(List continued on next page.)

*Primary Examiner*—Gollamudi S. Kishore
*Attorney, Agent, or Firm*—Bromberg & Sunstein

[57] ABSTRACT

This invention relates to a method of directing a therapeutic agent to selected cells, wherein a complex is formed between a polysaccharide capable of interacting with a cell receptor and a therapeutic agent. The resulting complex is administered to a subject, and permitted to be internalized into the selected cells through a process known as receptor mediated endocytosis (RME). The polysaccharide may be, for example, arabinogalactan, gum arabic, mannan or hydrolysis products thereof; the therapeutic agent may be, for example, an antiviral agent, a nucleic acid, hormone, steroid, antibody, chemoprotective or radioprotective agent. The cell receptor may be for example, the asialoglycoprotein receptor or the mannose receptor.

17 Claims, 4 Drawing Sheets

U.S. PATENT DOCUMENTS

| | | | |
|---|---|---|---|
| 4,609,640 | 9/1986 | Morishita et al. | 514/12 |
| 4,735,796 | 5/1988 | Gordon | 424/9 |
| 4,770,183 | 9/1988 | Groman et al. | 128/654 |
| 4,794,170 | 12/1988 | Fiume et al. | 530/363 |
| 4,804,529 | 2/1989 | Bardy et al. | 424/9 |
| 4,822,594 | 4/1989 | Gibby | 424/9 |
| 4,827,945 | 5/1989 | Groman et al. | 128/653 |
| 4,859,449 | 8/1989 | Mattes | 424/9 |
| 4,861,597 | 8/1989 | Kida et al. | 424/450 |
| 4,946,675 | 8/1990 | Baldwin | 514/2 |
| 4,946,830 | 8/1990 | Pulverer | 514/23 |
| 5,032,678 | 7/1991 | Washino | 534/14 |
| 5,041,541 | 8/1991 | Mazur | 536/11 |
| 5,129,877 | 7/1992 | Gallo | 600/12 |
| 5,284,646 | 2/1994 | Menz et al. | 424/9 |
| 5,336,506 | 8/1994 | Josephson | 424/488 |

OTHER PUBLICATIONS

1983 Lai et al., *J. App. Polymer Sci: Applied Polymer Symposium* 37:943–953.
1983 Wu et al., *Proc. Nat'l. Acad. Sci.* 80:3078–3080.
1985 Vera et al, *J. Nucl. Med.* 26:1157–1167.
1985 Wu et al., *Hepatology* 5:709–713.
1987 Fiume et al., *Cancer Drug Delivery* 4:145–150.
1987 O'Mullane et al., "Biopharmaceutics of Microparticulate Drug Carriers," *Ann. N.Y. Acad. Sci.* 507:120–140.
1988 Strye, *Biochemistry*, 3d ed., NY:W. N. Freeman Co., pp. 343–344.
1988 Kanke et al., *J. Parenteral Science and Technology* 42:157–165.
1988 Fiume et al., *Lancet* 2:13–15.
1989 Kiyohara et al., *Carbohydrate Research* 187:117–129.
1989 Duvallet et al., *Polymer Bulletin* 21:517.
1989 Meijer, *Pharm. Res.* 6(2):105–118.
1990 Molema et al., *Biochem. Pharm.* 40:2603–2610.
1990 Al–Deen et al., *J. Chromatography* 512:409–414.
1990 Meijer, *Trends in Drug Research*, vol. 13, pp. 303–332.
1990 Roche et al., *Res. Virol.* 141:243–249.
1991 Dickinson et al. in "Food Polymers, Gels and Colloids," *Special Publication No. 82*, Proceedings of an international symposium by the Food Chemistry Group of the Royal Society of Chemistry, Dickinson, ed., Norwich England.
1991 Schein, *International Conference on Chemical Modifiers of Cancer Treatment*, Clearwater FL, pp. 341–342.
1992 Meijer, *Antiviral Research*, 18:215–258.
Arabinogalactan for Hepatic Drug Delivery, Groman, et al., Bioconjugate Chemistry, vol. 5, No. 6, 1994, pp. 547–556.
Conjugation of Adenine Arabinoside 5'–Monophosphate to Arabinogalactan: Synthesis, Characterization, and Antiviral Activity, Enriquez, et al., Bioconjugate Chemistry, vol. 6, No. 2, 1995, pp. 195–202.
Abullah and Kierszenbaum (1989), J. Cell Biol. 108, pp. 367–375.
Blake, Clarke, and Jansson (1983), Carbohydr Res 115, pp. 265–272.
Bodmer and Dean (1985) Methods in Enzymology 112, pp. 298–306.
Brown et al., (1978) Arch. Bioch. Biophys. 188, pp. 418–428.
Chibata (1978), *Immobilized Enzymes*, Halstead Press, New York.
Clarke, Anderson, and Stone (1979), Phytochemistry 18, pp. 521–540y.
Degols, et al. (1989), Nucleic Acids Res 17, pp. 9341–9350.
Dragsten et al. (1987) Biochem. Biophys. Acta 926, pp. 270–279.
Fallon and Schwartz (1985) Hepatology 5, pp. 899–901.
Furuno, et al. (1983), J. Biochem 93, p. 249.
Glicksman, ed. (1982) "Food Hydrocolloids" CRC Press, p. 5 and p. 33.
Gorin and Barreto–Bergter in "The Polysaccharides," vol. 2, G. O. Aspinall, ed., Academic Press, 1983, pp. 376–380.
Hamstra et al. (1980) JAMA 243, pp. 1726–1731.
Hartford and Ashwell in "The Glycoconjugates," vol. IV, M. I. Horowitz, ed., Academic Press, 1982, pp. 27–55.
Henderson and Hillman (1969) Blood 34, pp. 357–375.
Hill, et al. (1987), Pigment Cell Res 1, pp. 81–86.
Hofnagel (1986), J. Hepatol. 3, pp. S73–S80.
Hubbard, et al. (1979), J. Cell Biol. 83, pp. 47–64.
Josephson, et al. (1990), Mag. Res. Imag. 8, pp. 637–646.
Kligerman, et al. (1991), 7th International Conference on Chemical Modifiers of Cancer Treatment, Clearwater, FL, pp. 338–340.
Lee et al. (1984) Biochemistry 23, pp. 4255–4261.
Lee, Haekyung, Kelm, Sorge, Teruo, Yoshino, and Schauer (1988), Roland Biol. Chem., Hoppe–Seyler 369, pp. 705–714.
Lok, et al. (1984), J. Antimicrob. Chemother. 14, pp. 93–99.
Martin, C. R. (1976) "Textbook of Endocrine Physiology," Williams & Wilkins, p. 21.
Meizer and van der Sluijs (1989), Pharm. Res. 6, pp. 105–118.
Mukhopadhyay et al. (1989) Science 244, pp. 705–707.
Piper, et al. (1969), J. Med. Chem. 12, pp. 236–243.
Ranade, V. V. (1989), J. Clin. Pharmacol. 29, pp. 685–694.
Roitt (1991), *Essential Immunology*, Blackwell Scientific, London, p. 28.
Samoloski and Daynes (1985), Proc. Nat. Acad. Sci. 82, pp. 2508–2512.
Schein (1991), International Conference on Chemical Modifiers of Cancer Treatment, Clearwater, FL, pp. 341–342.
Schor, et al. (1990), Biochem J. 267, pp. 291–296.
Stockert and Becker (1980) Cancer Res. 40, pp. 3632–3634.
The Pink Sheet, Feb. 3, 1992, 54, #5.
van der Sluijs, et al. (1991), *Liver Diseases, Targeted Diagnosis and Therapy Using Specific Receptors and Ligands,* Marcel Dekker Inc., pp. 235–264.
Wileman et al. (1985) Biochem. J. 232, pp. 1–14.
Wong (1991), *Chemistry of Protein Conjugation and Cross–Linking,* CRC Press, Boca Raton.
Wu, et al. (1987), J. Biol Chem. 262, pp. 4429–2232.
Wu, et al. (1991), Hepatology 13, pp. 575–580.
Wu and Wu (1988) J. Biol. Chem. 263, pp. 14621–14624.

1. SYNTHESIS OF 'AMINO' RME POLYSACCHARIDE

RME-POLYSACCHARIDE-CO$_2$H + H$_2$N(CH$_2$)$_2$NH$_2$ $\xrightarrow{\text{EDC}}$ RME-POLYSACCHARIDE-C(=O)-NH(CH$_2$)$_2$NH$_2$ RME-POLYSACCHARIDE-CO$_2$H ==> POLYSACCHARIDE CONTAINING ACID GROUP (EITHER FROM SYNTHESIS IN FIG.3 OR NATURALLY OCCURING, eg. GUM ARABIC)

EDC ==> 1-ETHYL-3(3-DIMETHYLAMINOPROPYL) CARBODIIMIDE

2. SYNTHESIS OF THERAPEUTIC AGENT-RME-POLYSACCHARIDE COMPLEX

RME-POLYSACCHARIDE-C(=O)-NH(CH$_2$)$_2$NH$_2$ + araAMP ⟶

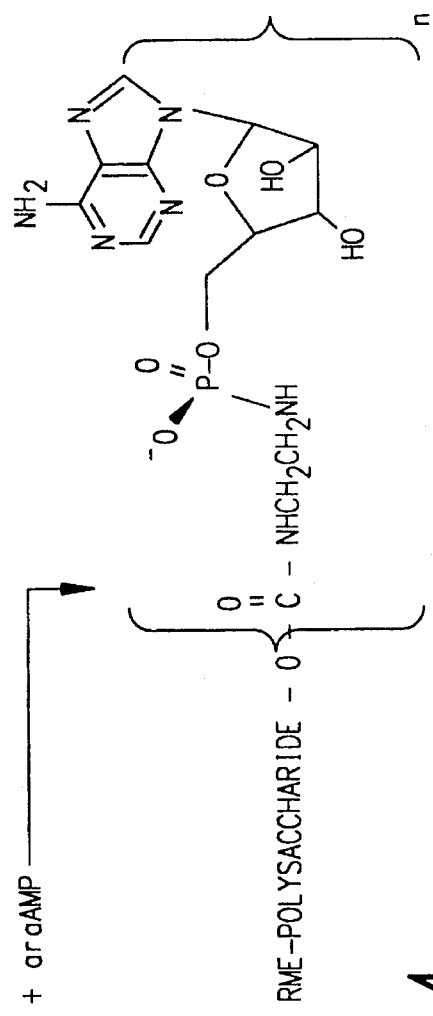

FIG.4

DELIVERY OF THERAPEUTIC AGENTS TO RECEPTORS USING POLYSACCHARIDES

CROSS REFERENCES TO RELATED APPLICATIONS

This application is a continuation-in-part of application Ser. No. 900,686, filed Jun. 17, 1992 now U.S. Pat. No. 5,478,576 which is a continuation-in-part of application Ser. No. 936,873, filed Aug. 27, 1992, now U.S. Pat. No. 5,336,506 which is a continuation of Ser. No. 630,017, filed Dec. 19, 1990, now abandoned, which is a continuation in part of Ser. No. 679,526 filed Apr. 2, 1991, now U.S. Pat. No. 5,141,739, which is a continuation of Ser. No. 384,991, filed Jul. 2, 1989, now abandoned, which is a continuation in part of Ser. No. 228,640 filed Aug. 4, 1988, now abandoned, which is a continuation in part of Ser. No. 067,586, filed Jun. 26, 1987 now U.S. Pat. No. 4,827,945, which is a continuation in part of Ser. No. 882,044, filed Jul. 3, 1986, now U.S. Pat. No. 4,770,183, all of which are incorporated herein by reference.

TECHNICAL FIELD OF THE INVENTION

The present invention relates to methods for the targeting of a therapeutic agent to a specific population of cells, especially hepatocytes.

BACKGROUND OF THE INVENTION

The Need For Directing Therapeutic Agents to Selected Cells.

Therapeutic agents are agents administered with the intent of changing, in a beneficial manner, some physiological function of the recipient. Such agents can include drugs, proteins, hormones, enzymes, nucleic acids, peptides, steroids, growth factors, modulators of enzyme activity, modulators of receptor activity and vitamins. This invention involves directing therapeutic agents to selected cells (which is also called targeting), thereby increasing the concentration of therapeutic agent in some cells where the agent produces a beneficial effect and decreasing its concentration in cells where it produces a toxic effect. By directing the therapeutic agent toward certain cells where drug efficacy is to be obtained, and away from other cells where drug toxicity is obtained, the safety and efficacy of an agent can be improved.

In contrast to therapeutic agents, diagnostic contrast-type agents are administered with the intent of illuminating some physiological function, while leaving other physiological functions unaffected. These diagnostic agents include radioactive isotopes for scintigraphy, electron dense labels for X-ray or computer tomography, and magnetic labels for magnetic resonance imaging.

RES Based Targeting

One strategy of targeting therapeutic agents involves directing such agents to the phagocytic cells, called macrophages, which are found in high numbers in a series of organs referred to as the reticuloendothelial system (RES). Organs of the RES include the liver, spleen and bone marrow. Phagocytosis is a process whereby a wide variety of materials, including colloids, particles, liposomes and microspheres are non-specifically removed from the blood. For example, Imferon, a dextran coated colloidal ferric oxyhydroxide used for the treatment of anemia, is slowly cleared from the blood by the phagocytic activity of the macrophages of the RES. (Henderson et al., 34 Blood (1969) pp. 357–375.). Liposome encapsulated drugs have also been used to treat such diseases as Leishmania (O'Mullane et al "Biopharmaceutics of Microparticulate Drug Carriers," Ann. N.Y. Acad. Sci. (1987) 507:120–140) Microspheres have also been employed to deliver agents to the RES, often to stimulate the immune function of macrophages (Kanke et. al. "Interaction of Microspheres with blood constituents, III. Macrophage phagocytosis of various types of polymeric drug carriers," 42 J. Parenteral Science and Technology (1988) pp. 157–165). However, directing therapeutic agents to macrophages is of little use in many diseases that do not involve macrophages or macrophage function.

RME Based Targeting

A second strategy for targeting therapeutic agents to macrophages involves attaching agents to molecules (termed carriers) that are withdrawn from the vascular compartment by receptor mediated endocytosis (RME). RME is a process whereby molecules in the extracellular space bind to specific receptors on the cell surface and are internalized. The uptake of substances by RME is a feature of normal, healthy cells. RME transport systems can be found on normal macrophages, hepatocytes, fibroblasts and reticulocytes. RME enables cells to remove a variety of macromolecules from plasma, such as low density lipoproteins, transferrin and insulin. See Table 1 of Wileman et al., 232 Biochem. J. (1985) pp. 1–14 for a list of cells performing RME, which also contains a general review of RME. See also Table I of Menz, E. T., PCT WO 90/01295, filed Aug. 3, 1989, both incorporated herein by reference. By attaching therapeutic agents to carriers undergoing RME, therapeutic agents can be directed to cells which do not perform phagocytosis, e.g., hepatocytes of the liver. Targeting therapeutic agents based on RME requires the attachment of therapeutic agents to satisfactory carrier molecules, which then alter the biodistribution of the therapeutic agent.

Diagnostic agents have also been attached to carriers that that undergo uptake by RME, for example, carriers that interact with asialoglycoprotein receptor such as, radioisotope preparations of neoglycoalbumin-$^{99}$Tc have shown high liver specificity in animal studies (Vera et al, J. Nucl. Med. 26:1157–1167 1985). In another example, Groman et al, (U.S. Pat. No. 5,284,646, incorporated herein by reference) conjugated superparamagnetic metal oxides to glycoproteins for use as an in vivo contrast agent in magnetic resonance imaging.

Carriers For RME Targeting

One type of molecule widely employed as carriers for delivering therapeutic agents based on RME are glycoproteins. A glycoprotein molecule consists of a protein backbone that is associated with multiple oligosaccharide side chains, which often consist of between 2 and 20 monosaccharides covalently linked to the protein backbone by either an N-linkage or an O-linkage (Stryer L, Biochemistry, 3d Ed., N.Y.: W. N. Freeman Co., pp. 343–344 (1988)). For example, a receptor known as the asialoglycoprotein receptor on hepatocytes recognizes glycoproteins possessing galactose residues and interalizes them. Those glycoproteins that have a sialic acid attached to a penultimate galactose on the associated oligosaccharides lack an affinity for the receptor, but can be converted to receptor binding molecules by removal of the terminal sialic acid to expose the galactose. For example, fetuin can be converted to asialofetuin by removal of the terminal sialic acid groups. Recognition by the asialoglycoprotein receptor, which performs RME, is dependent on the number and clustering arrangement of the galactosyl linkages on the oligosaccharide. Similarly, the mannose receptor on macrophages recognizes glycoproteins possessing mannose residues and internalizes them by RME.

An alternative to glycoprotein carriers are the so-called neoglycoproteins, which are synthesized when multiple mono- or disaccharides are covalently attached to protein molecules. An example of a neoglycoprotein is lactosylated bovine serum albumin, which binds to the asialoglycoprotein receptor on hepatocytes.

Table 1 provides selected examples of the receptors, cells, therapeutic agents and carriers involved with RME based targeting. For further reviews see Ranade, J. Clin. Pharmacol. 29:685–694 (1989); and Bodmer et al., Methods of Enzymology vol. 112., p. 298, Academic Press (1985). For recent reviews, see Meijer, Antiviral Research, 18:215–258 (1992); Meijer, Trends in Drug Research, vol 13, 303–332; Meijer, Pharm. Res. 6(2):105–118 (1989).

expose the galactose residue, is required for the glycoprotein to interact with the asialoglycoprotein receptor. For example, fetuin must be desialylated to produce a carrier that can interact with the receptor. Similarly, neoglycoproteins are synthesized by attaching multiple lactose residues to albumin.

2. Glycoproteins derived from bovine sources can be immunogenic in humans. Neoglycoproteins have been reported to be immunogenic in animals (Fiume L., Busi C., Preti P., Spinosa G. Cancer Drug Delivery, 1987, 4:145–150).

TABLE 1

RME Based Targeting:
Receptors, Cells, Therapeutic Agents and Carriers

| Receptor/Cell | Therapeutic Agent/Carrier | Reference |
| --- | --- | --- |
| Galactose or Asialoglycoprotein/ Hepatocytes | ara AMP/lactosylates human serum albumin | Fiume et al., Lancet 2:13–15 (1988) |
| Galactose or Asialoglycoprotein/ Hepatocytes | acetylcyteine/asialofetuin | Wu and Wu, Hepatology 5 709–713 (1985) |
| Galactose or Asialoglycoprotein/ Hepatocytes | folinic acid/asialofetuin | Wu and Wu, Proc. Natl Acad. Sci. 80:3078–3080 (1983) |
| Galactose or Asialoglycoprotein/ Hepatocytes | DNA/asialoorosomucoid | Wu and Wu, J. Biol. Chem. 263:14621–14624 (1988) |
| Mannose/T4 lymphocytes | AZT/mannosylated albumin | Molema et al, Biochem. Pharm. 40 2603–2610 (1990) |
| Mannose/macrophage | muramyl dipeptide/mannosylated albumin | Roche et al., Res. Virol. 141, 243–249. |

Features of RME

Uptake by RME exhibits three properties characteristic of ligand-receptor interactions generally: structural specificity, saturability and competition.

Structural specificity is observed when a receptor can distinguish between closely related structures and only molecules with structures meeting the binding requirements of the receptor binding site are internalized. Often the receptors involved in RME are discovered by their ability to internalize or clear glycoproteins from circulation.

Saturability is observed when the rate of an agent internalized via RME decreases with increasing concentrations of that agent. This results because, at high concentrations, the receptor approaches full occupancy or becomes saturated with ligand.

Competition is observed when the removal from the blood (clearance) of an molecule can be reduced by the presence of a second molecule bearing a structural resemblance to the first agent. The second molecule competes for receptor binding sites and decreases the rate of internalization of the first agent. Whereas saturability occurs when high concentrations of a single ligand compete for a limited number of receptor sites, competition results when chemically different ligands bind to a limited number of receptor sites. Competition is used to distinguish RME type polysaccharides of the invention from other types of polysaccharides (see Table 2).

Problems with Glycoproteins and Neoglycoproteins as Carriers for Therapeutic Agents In spite of the many cases where glycoproteins and neoglyproteins have been used as carriers of therapeutic agents, these carriers are subject to several problems, some of which have been discussed in the literature.

1. Glycoproteins and neoglycoproteins undergoing RME are not naturally occuring materials. Modification of the glycoprotein, such as the removal of a terminal sialic acid to 3. Neoglycoproteins and glycoproteins generally will not tolerate organic solvents during conjugate synthesis. Organic solvents are employed in the examples of the invention.

4. With the synthesis of neoglycoproteins, the positively charged amine groups of proteins are utilized (and neutralized), for the attachment of mono or disaccharide. As a result, the neoglycoprotein is often strongly negatively charged. Such strong negative charge facilitates uptake by so-called scavenger receptors, and decreases the amount of therapeutic agent delivered to cells by RME (Kanke M., Geissler R. G., Powell D., Kaplan A., DeLuca P. J. Parenteral Science and Technology, 1988, 42:157–165).

For the foregoing reasons, there is a need for new approaches to direct therapeutic agents to selected cells, a need which could be met if improved carriers for delivering therapeutic agents to cells performing RME could be found. Such carriers should have a high affinity for the receptor, and maintain that affinity after complex formation and attachment of the therapeutic agent. In addition, the desired carrier should be naturally occurring, be readily available in pure form, and must be nontoxic.

SUMMARY OF THE INVENTION

It is the object of the present invention to provide a method for directing a therapeutic agent to selected cells by administering to a subject, an effective amount of a complex, wherein the complex comprises the therapeutic agent conjugated to an RME polysaccharide; and permitting the binding of the conjugated RME polysaccharide to an RME receptor on the cell target so as to internalize the therapeutic agent within the cell target.

The RME polysaccharide can be, for example arabinogalactan, gum arabic or mannan. The therapeutic agent can be, for example, an antiviral agent, hormone, a vitamin, antibody, enzyme or gene. In another embodiment, the RME polysaccharide can be a hydrolysis product of another RME polysaccharide.

BRIEF DESCRIPTION OF THE DRAWINGS

FIG. 4 details the chemistry for attaching a therapeutic agent to an RME polysaccharide through amine groups on the RME polysaccharide.

DETAILED DESCRIPTION OF THE SPECIFIC EMBODIMENTS

Figure 1:
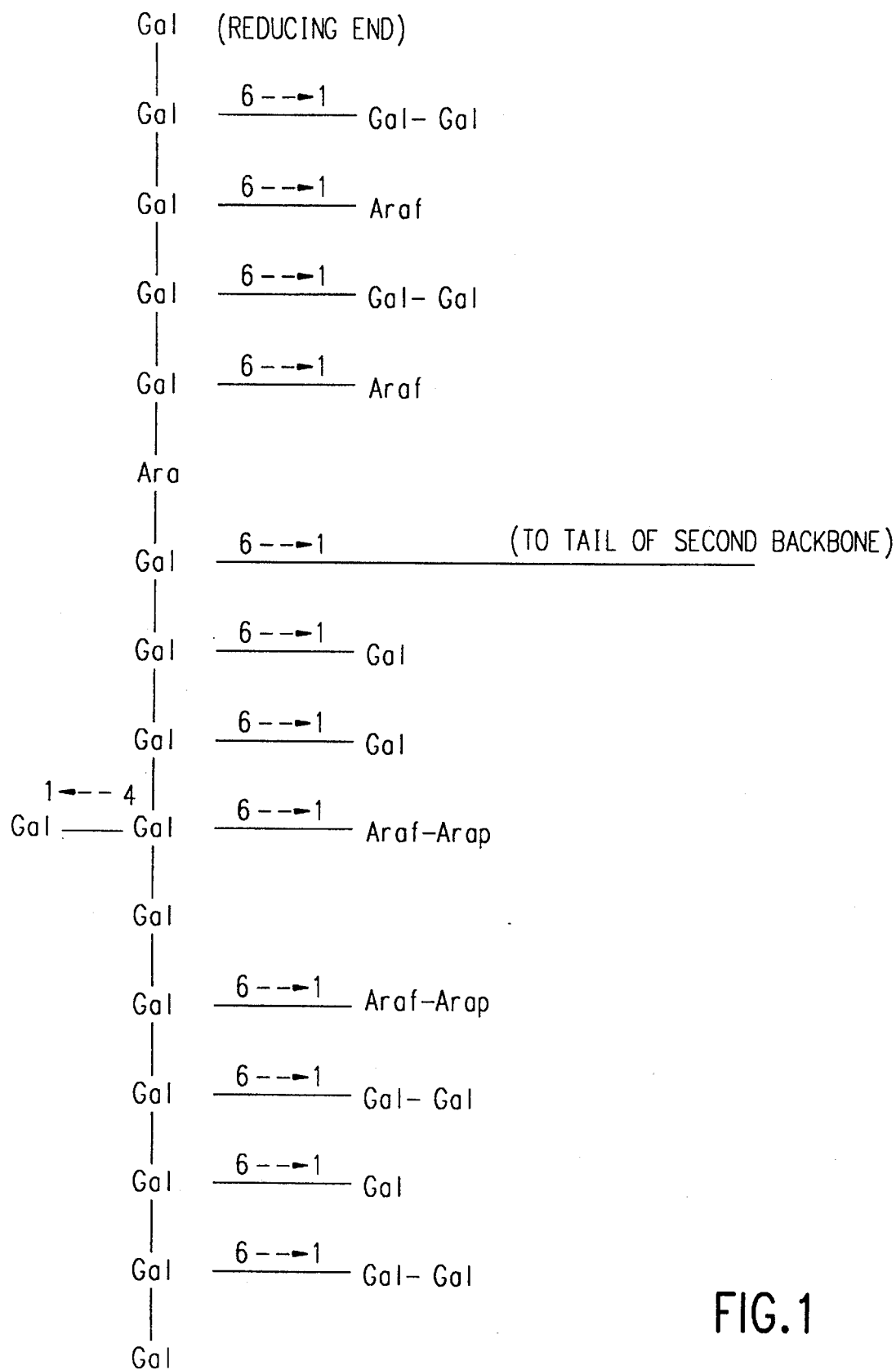
FIG. 1 shows the generalized structure of the RME polysaccharide arabinogalactan.

This invention is directed to the use of polysaccharide carriers for directing therapeutic agents to selected cells, and away from other cells, and in so doing, provides a method of targeting a therapeutic agent into selected cells via receptor mediated endocytosis (RME). Targeting increases the concentration of the therapeutic agent in cells where the agent exerts some beneficial or diagnostic action and reduces its concentration in other cells where unwanted, toxic effects are being produced. Many therapeutic agents produce toxic effects, not upon the cells where the agent has a beneficial action, but on cells other than those in need of the beneficial action.

By using a polysaccharide carrier for directing therapeutic agents to selected cell, and away from other cells, the invention provides a way of improving the safety and efficacy of previously developed therapeutic agents. For example, a therapeutic agent intended to inhibit the replication of hepatitis B virus in the hepatocytes of the liver, may exhibit toxic effects in bone marrow cells. Since bone marrow function is essential for life, toxic effects on marrow limit the dose of the agent that can be given to a patient. However, according to an embodiment of the invention, targeting the agent to hepatocytes by attachment to a carrier capable of uptake by RME causes the reduction in the concentration of the agent delivered to bone marrow. Furthermore, the potency of the agent is improved, because the fraction of the therapeutic agent which normally goes to bone marrow is now directed to the liver. Bone marrow related side effects can thus be significantly reduced.

The RME-Polysaccharides of the Invention

We have found that some polysaccharides interact with receptors involved in RME, which we refer to as RME-polysaccharides. RME polysaccharides are naturally occurring polysaccharides obtained from natural sources. Examples include arabinogalactan and gum arabic, which interact with the asialoglycoprotein receptor of hepatocytes, and mannan which interacts with the mannose receptor (Table 1). Common polysaccharides including celluloses, starches, hydroxyethyl starches, heparins, dextran sulfates, carboxylmethylated dextran and carboxymethyl cellulose do not interact with receptors involved in RME.

Characteristics of RME Polysaccharides

RME-polysaccharides are often highly branched structures. Many backbone residues have at least three branch points, and the branching occurs in a way that produces numerous terminal monosaccharide residues. Ultimately, it is the type, number, and arrangement of these terminal monosaccharide residues that determine the strength of the interaction between the RME polysaccharide and the receptor. For a polysaccharide to be useful as a carrier, there must be multiple monosaccharides in the proper arrangement for a useful interaction with the receptor. In the case of the asialoglycoprotein receptor, multiple, clustered galactose residues produce useful receptor binding. For example, the RME polysaccharide arabinogalactan is highly branched with numerous terminal galactose residues in close proximity to each other and shows a strong interaction with the asialoglycoprotein receptor, see Table 2. In contrast, galactan, though composed of galactose, shows very little interaction with asialoglycoprotein receptor. This is because galactan is a linear polymer with few terminal galactoses. As indicated by the poor receptor recognition of galactan, RME polysaccharides cannot be determined from compositional data alone.

Test for RME Polysaccharides

Polysaccharides can be classified as RME- polysaccharides or non RME polysaccharides based on their ability to compete for binding with a second substance known to bind to an RME receptor. For example, the ability of polysaccharides to interact with the asialoglycoprotein receptor can be demonstrated by competition assays in which the ability of the polysaccharides to slow the removal (clearance) of arabinogalactan-coated superparamagnetic iron oxide colloid previously shown to be cleared by that receptor, can be demonstrated. Since this colloid has been shown to be cleared by the asialoglycoprotein receptor (Josephson et al., Mag. Res. Imag. 8:637–646 (1990); Menz, E. T., PCT WO 90/01295, filed Aug. 3, 1988, both incorporated herein by reference), polysaccharides that interact with the receptor slow the clearance of the colloid, i.e. increase blood half-life.

To obtain the blood half-life, a Sprague Dawley rat (200–300 g) was anesthetized and injected with a defined dose of blocking agent (such as arabinogalactan or galactan), followed by an injection of the colloid at 40 μmoles Fe/kg. Blood was withdrawn at various times, and $1/T1$, the spin-lattice relaxation rate, and the $1/T2$, the spin-spin relaxation rate, were determined. The enhancement in $1/T1$ and $1/T2$ are related to the concentration of superparamagnetic iron oxide. From changes in $1/T1$ or $1/T2$, the blood half-life of the arabinogalactan-coated superparamagnetic metal oxide was determined. The rate of clearance of the arabinogalactan-coated superparamagnetic iron oxide colloid alone was used as a reference point. An increase in the colloid half-life (reduced clearance) after administration of the blocking agent was indicative of the binding of the blocking agent to the same receptor as the colloid, thereby blocking the uptake of the colloid. In the absence of a blocking agent, superparamagnetic iron oxide colloid was rapidly cleared via the asialoglycoprotein receptor, with a blood half-life of 2.8 minutes. The results are shown in Table 2.

TABLE 2

Effect of Polysaccharides on Clearance of Superparamagnetic Iron Oxide Colloid

| Blocking Agent | Type | Blocking Agent Dose (mg/kg) | Colloid Blood Half-life (min) |
|---|---|---|---|
| None | — | none | 2.8 |
| Arabinogalactan | RME-polysaccharide | 150 | 33.2 |
| Gum arabic | RME-polysaccharide | 150 | 107.5 |
| Asialofetuin | Glycoprotein | 100 | 56.6 |
| Hydroxyethyl ethyl starch | Non-RME polysaccharide | 750 | 1.6 |
| Galactose | Monosaccharide | 300 | 6.0 |

The RME-polysaccharides (arabinogalactan and gum arabic) and the glycoprotein carrier asialofetuin increased the blood half-life of the superparamagnetic iron oxide colloid, indicating that the colloid and the test carrier were competing for the same receptor binding sites. In comparison, the non-RME polysaccharide hydroxyethyl starch and the monosaccharide galactose showed little effect on the half-life of the colloid. In a manner similar to the experiment performed in Table 2, the RME polysaccharide mannan blocked the clearance of radioactive glycoprotein, RNase B. Brown et al., Arch. Biochem. Biophys. 188:418–428 (1978). This was due to clearance of RNase B by a mannose recognizing receptor and indicates that mannan is an RME-type polysaccharide.

The competitive clearance assay above can also be used to determine if the RME-polysaccharide-therapeutic agent complexes synthesized, such as those in the examples below, maintain their interaction with the receptor.

RME- polysaccharides can be subjected to partial hydrolytic digestion, to produce lower molecular weight RME-polysaccharides. Starting with an RME-polysaccharide, acid catalyzed, base catalyzed or enzyme catalyzed hydrolysis may be used to produce lower molecular weight polysaccharides. The resulting polysaccharides are then assessed for their ability to interact with receptors, for example by using the assay of Table 2. The polysaccharides of the invention, before or after hydrolytic digestion, have molecular weights greater than about 1,000 daltons.

Advantages of RME Polysaccharides as Carriers of Therapeutic Agents

RME-polysaccharides have several advantages as carriers of therapeutic agents.

1. RME polysaccharides are recognized by receptors in the their natural form. Modifications of naturally occurring glycoproteins, (removal of sialic acid) or synthetic reactions to yield neoglycoproteins (attaching lactose to albumin) are required for such molecules to serve as carriers of therapeutic agents.

2. Polysaccharides have high chemical stability. Because of the stability of polysaccharides, covalent linkages between therapeutic agents and polysaccharides can be achieved in organic solvents. This is a considerable advantage since some therapeutic agents have low water solubility. Working in nonaqueous media, water-labile linkages (e.g., esters) can be created between the therapeutic agent and the polysaccharide. An example of such chemistry is provided in Example 6. In addition, polysaccharides do not denature at high temperature, and tolerate extremes of pH or in organic solvents. In Example 1, the polysaccharide arabinogalactan is used as a coating for an iron oxide colloid. During that synthesis, arabinogalactan is exposed first to a pH below about 3, when soluble iron salts are present, then to a high pH after base addition and finally to a high temperature.

3. RME polysaccharides can be obtained from non-animal, natural (i.e., microbiological or plant) sources. Glycoproteins from human or animal sources may contain pathogens whose absence is costly to assure.

4. Plant or microbiological sources can provide crude polysaccharide preparations on a large scale, in a reliable manner and at a reasonable price.

Examples of RME Polysaccharides

1. Arabinogalactans.

Arabinogalactans are a class of polysaccharides that may be obtained from the cell walls of many species of trees and plants. A common source of arabinogalactan is the American western larch (*Larix occidentalis*). Arabinogalactan from this source has been used as a binder, emulsifier or stabilizer in foods.

Arabinogalactan consists of a galactose backbone with branched chains of arabinose and galactose. Generally, the ratio of galactose to arabinose is between 5:1 and 10:1. The molecular weight ranges from 10 to 100 kilodaltons (Glickman, ed , "Food Hydrocolloids," CRC Press (1982) pp. 5, 33). Glycosyl linkage analysis of arabinogalactan is consistent with a highly branched structure comprising a backbone of 1,3 linked galactopyranose connected by 1,3Êglycosidic linkages, comprised of 3,4,6-, 3,6-, and 3,4-as well as 3-linked residues. In the carbon-13 NMR spectra, the major resonances of arabinogalactan are assigned to §-galactopyranose, §-arabinofuranose, and §-arabinopyranose. FIG. 1 shows a representation of the structure of arabinogalactan.

In embodiments of the invention as described in the examples, commercially available arabinogalactan (from Sigma Chemicals) has been further purified by ultrafiltration to remove impurities greater than 100,000 daltons and smaller than 10,000 daltons.

2. Gum Arabic.

Gum Arabic is a highly branched polysaccharide obtained from the exudate of *Acacia senegal (L) Willd*. A naturally occurring gum arabic molecule consists of 1,3-linked D-galactopyranose units, some of which are substituted at the 6-position with side chains of 1,6-linked galactopyranose units terminating in glucuronic acid or 4-O-methylglucouronic acid residues. Small amounts of polypeptides (about 2%), are present in crude gum, mostly in the form of serine and hydroxyproline (Dickinson et al. in "Food polymers, gels and colloids, Special publication No. 82, Proceedings of an international symposium by the Food Chemistry Group of the Royal Society of Chemistry, Dickinson, Ed., Norwich England (1991)). Various authors report a molecular weight for the crude Gum Arabic ranging from 720,000 daltons (with protein) (Duvallet et al. Polymer Bulletin 21:517 (1989)) to approximately 300,000 daltons (see Dickinson, above). Controlled degradation using pronase reduces the molecular weight to approximately 180,000 daltons (see Duvallet). Commercially available material has a molecular weight in the range of 250,000 daltons.

The gum arabic used in the embodiments of the invention was obtained from Sigma Chemicals and has a molecular weight of approximately 150,000 to 300,000 daltons by size exclusion chromatography. Commercial gum arabic is comprised primarily of arabinose, galactose, rhamnose and glucuronic acid, and has a nitrogen content <0.5%. There are approximately 176Êcarboxylic acidsÊper mole of gum arabic by acid titration, and approximately 250 carboxylic acids by base titration. These carboxylic acid groups facilitate the derivatization procedures.

Embodiments of the invention also include derivatives of gum arabic, such as fragments, dimers, trimers, and polymers of gum arabic, that retain RME receptor recognition. These derivatives provide a substrate for attaching therapeutic agents through attachment to the amino, carboxyl, sulfhydryl, phosphoryl or other functional groups of the derivative. The carboxyl groups that naturally occur on the terminal glycoside of gum arabic can be used to attach other molecules through the use of carbodiimides or other agents. Amine derivatives can also be used to attach therapeutic agents by a variety of reactions. Alternatively, dextran or poly-L-lysine can be attached to the gum arabic carrier to provide an increased number of sites of attachment for the therapeutic agent. The derivatives are produced in such a way as to maintain asialoglycoprotein receptor recognition.

Figure 2:
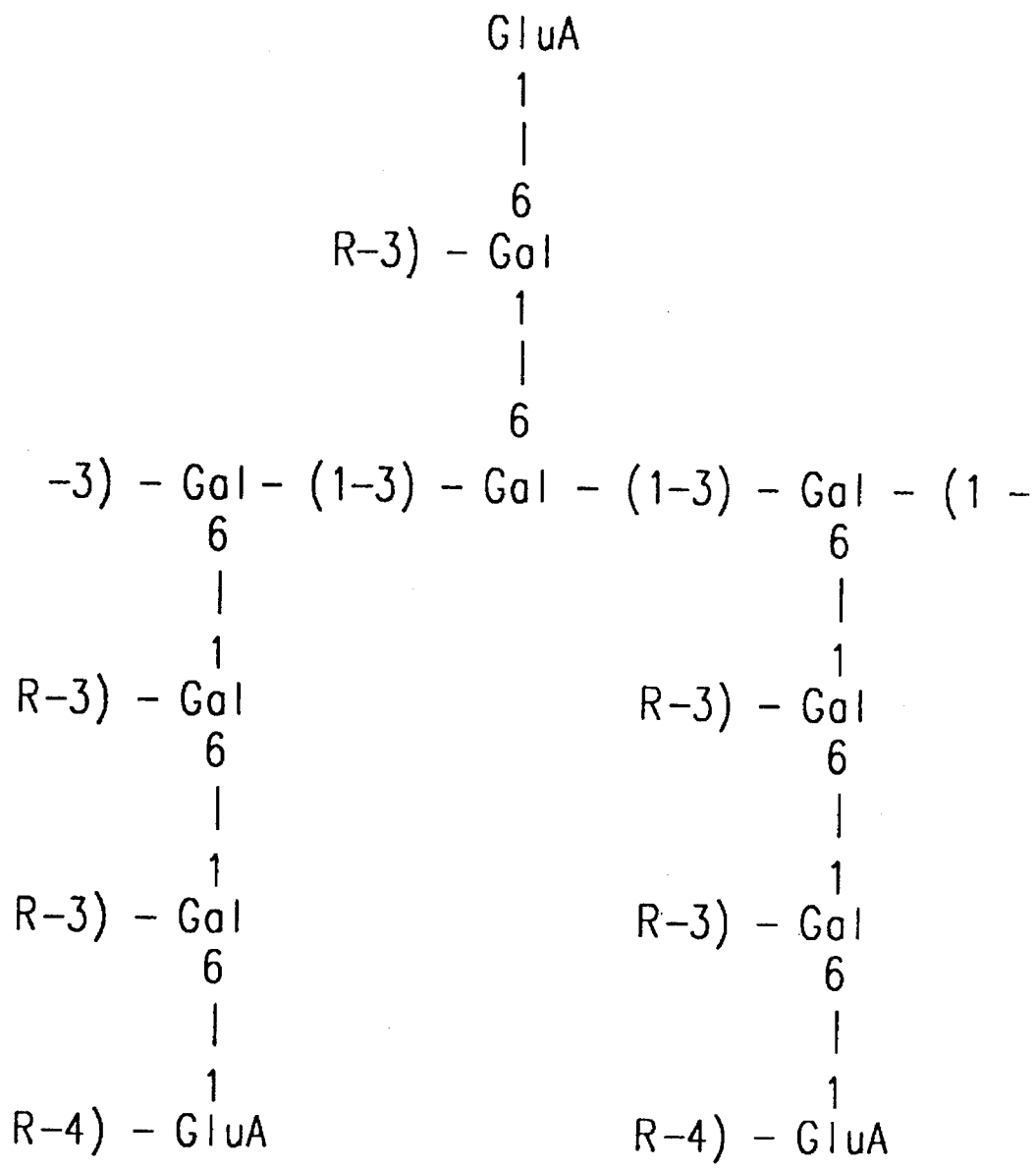
FIG. 2 shows the generalized structure of the RME polysaccharide gum arabic.
Figure 3:
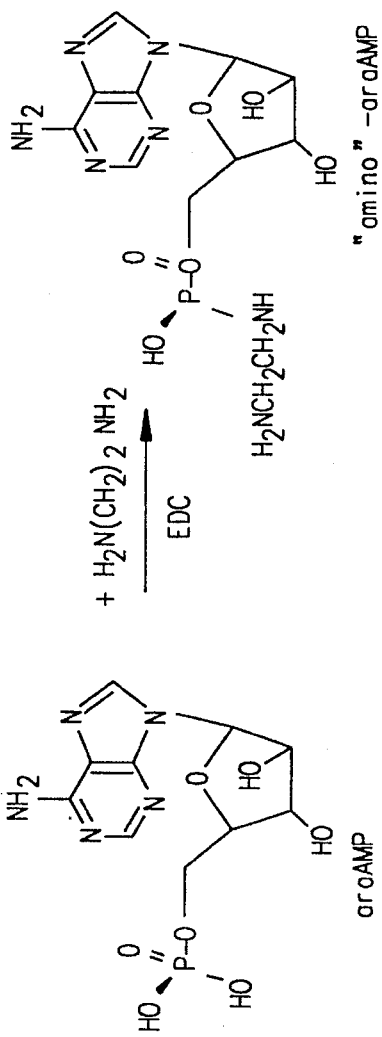
FIG. 3 details the chemistry for attaching a therapeutic agent to an RME polysaccharide through carboxyl groups on the RME polysaccharide.
Figure 3:
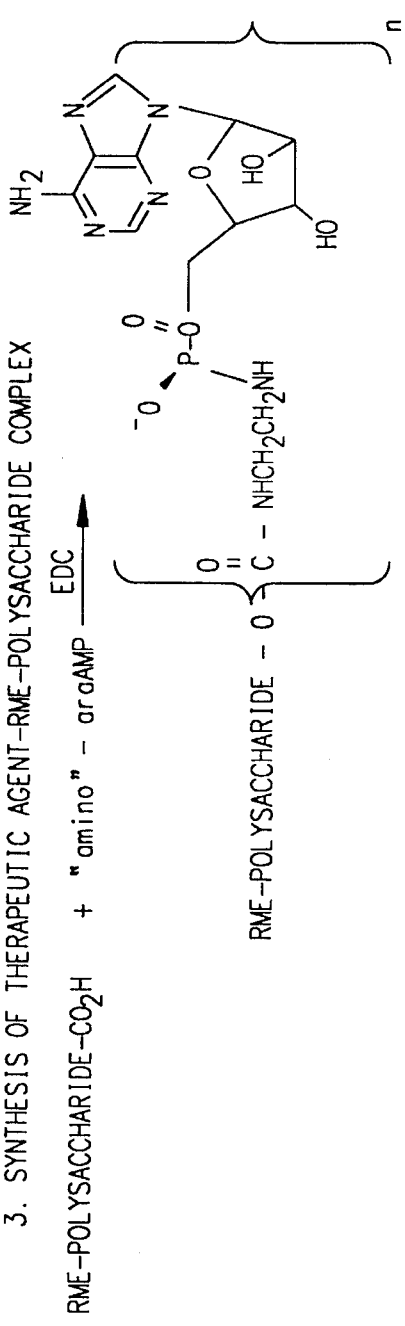
Figure 3:
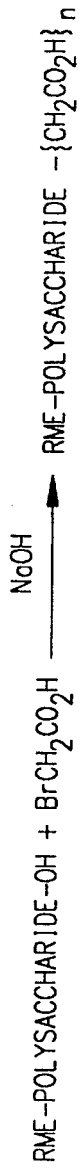

We have surprisingly shown that gum arabic can tolerate a substantial degree of modification, and yet retain binding affinity for RME receptors. This is compatible with our findings reported above for arabinogalactan. The ability to modify gum arabic while retaining its biological activity permits its use as a carrier for a wide variety of therapeutic agents using targeting strategies. FIG. 2 shows a representation of the structure of gum arabic.

3. Mannans.

Mannans are a class of polysaccharides that can be obtained from the cell walls of yeast. They are predominantly -D-mannopyrans with a variety of linear and branched chain structures (Gorin et al., Vol. 2 "The Polysaccharides," G. O. Aspinall, ed., Academic Press (1983) pp. 376–380).

Mannans bind to the mannose receptor found on the macrophages of the RES. Therapeutic agents attached to mannan are consequently targeted to RME receptors on macrophages for uptake and internalization by RME.

Therapeutic Agents That Can Be Delivered by RME Polysaccharides

Utilizing the methods of the invention, a wide variety of therapeutic agents may be directed to selected cell targets. The examples described below and listed in Table 3 show how RME polysaccharides and derivatives may be conjugated to therapeutic agents produce a variety of molecules that can be directed to selected cells. FIGS. 3 and 4 depict two types of chemistries for attaching therapeutic agents to the carrier. Therapeutic agents that can be used with the carrier of the invention include hormones, steroids, vitamins, nucleic acids, enzymes, chemoprotective agents, radioprotecting agents, antibodies, and antiviral agents. For example, antiviral agents, such as nucleotide and nucleoside analogs, conjugated to RME polysaccharides can be delivered to those cells bearing RME receptors in which viral replication occurs (hepatocytes).

Ara-AMP, a nucleotide analog, is an example of an antiviral drug having limited utility because of adverse side effects caused by the therapeutic agent at sites distant to the target site. Studies on the use of Ara-AMP for the treatment of hepatitis B, revealed serious neurological side effects. (Lok et al., J. Antimicrob. Chemother. 14:93–9 (1984); Hoffnagel et al., J. Hepatol. 3:S73–80 (1986)). By forming an Ara-AMP-RME polysaccharide conjugate, unwanted side effects of the therapeutic agent at non-target sites may be minimized by reducing the concentration of the drug in the central nervous system and increasing the concentration of the drug in the target organ where viral replication is localized. Ara-AMP has been coupled to a glycoprotein recognized by the asialoglycoprotein receptor (U.S. Pat. No. 4,794,170) but this form of carrier has limitations as listed above. Other antiviral therapeutic agents which may be coupled to RME-polysaccharides to improve the safety and efficacy of the therapeutic agent include acyclovir, the nucleoside analog Ara-A and interferons.

Another class of antiviral therapeutic agents are antibodies and antibody homologs, including polyclonal antibodies, monoclonal antibodies, and antibody fragments. Following infection with a virus, circulating antibodies are produced in the blood by the host animal together with a cell mediated immune response. However, circulating antibodies can often be ineffective against viruses, which replicate inside cells. In the case of hepatitis B virus, viral replication occurs within the hepatocytes of the liver and antibodies to hepatitis virus antigens cannot directly bind the virus during this replication phase. By conjugating Hepatitis B antibody to RME polysaccharides, and permitting the conjugated antibody to bind to the asialoglycoprotein receptor, receptor mediated endocytosis is utilized and the antibody is able to enter the cytoplasm of the cell and bind viral antigen thereby becoming an effective therapeutic agent.

RME polysaccharides or RME derivatives can also serve as a carrier for radioprotecting therapeutic agents. One such agent, WR 2721, has been the subject of recent clinical studies to ascertain whether it can be used to protect the normal cells of cancer patients during radiotherapy (Kligerman et al., 7th International Conference on Chemical Modifiers of Cancer Treatment, 1991, Clearwater Fla., pp. 338–340) or chemotherapy (Schein, International Conference on Chemical Modifiers of Cancer Treatment, 1991, Clearwater Fla., pp. 341–342). However, recent evidence suggests that WR 2721 also protects cancer cells from radiation, which limits its use as a chemoprotecting agent (The Pink Sheet, Feb. 3, 1992, 54, #5). Forming a conjugate between, for example, gum arabic and WR2721 causes the radioprotecting agent to be directed to cells possessing the asialoglycoprotein receptor, that is, non-cancerous hepatocytes. In addition to WR2721, other free radical scavengers can be attached to RME polysaccharides, and targeted to receptor-bearing cells. Examples include selenium, melanins, cysteamine derivatives, phenolic functional groups (such as 6-hydroxy-chroman-2 carboxylic acids (e.g., Trolox) and tocopherols (e.g., Vitamin E), and enzymes (superoxide dismutase).

A further embodiment of the invention is a composition comprising RME-polysaccharides and poly-L-lysine, in which the strong positive charge of poly-L-lysine can cause some agents such as negatively charged nucleic acids to adhere by Coulombic effects (Wu et al., J. Biol. Chem. 262:4429–2232 (1987). For example, poly-L-lysine-gum arabic conjugates may be used as a carrier for genes or antisense oligonucleotides used in parenteral administration (Degols et al., Nucleic Acids Res. 17:9341–50 (1989)). The delivery of nucleic acids to target cells has utility in the treatment of genetic defects such as the deficiency of a hepatic enzyme in the liver. In these circumstances, DNA may be delivered to the liver so as to reverse the genetic defects. In addition to poly-L-lysine, other polymeric molecules, such as dextrin, dextran, or albumin may be coupled to RME polysaccharides.

In Example 1, an arabinogalactan colloid has been synthesized which acts as a carrier for iron and directs the iron to the hepatocytes via the RME receptor. Parenterally administered iron has often been used in the treatment of anemia, in the form of an iron oxide dextran complex called Imferon. The iron oxide dextran is slowly removed from blood by the RES. Imferon exhibits some tendency to produce adverse reactions caused by non-specific uptake by cells in vivo (Hamstra et al., 243 JAMA (1980) pp. 1726–1731). In contrast, iron oxides conjugated to the carrier, arabinogalactan (see Example 1) are delivered to target hepatocytes of the liver and rapidly internalized by RME (Menz et al, WO 90/1295).

In a further embodiment of the invention, vitamins have been delivered to specific RME cells. Example 3 shows the preparation of a folinic acid arabinogalactan conjugate, which delivers the vitamin folinic acid to hepatocytes via RME. An example of a drug that is chemically similar to folinic acid is that of methotrexate. Like folinic acid, methotrexate can be coupled to arabinogalactan by minor modifications of the procedure described in Example 3.

Examples 5 and 6 describe the targeted delivery of two steroidal hormones-estrogen and prednisolone to RME receptors on selected cells. Other steroids that may be effectively delivered in this manner include glucocorticosteroid. The targeting of steroids to cells has significant utility in the treatment of a range of diseases. (Martin, C. R., "Textbook of Endocrine Physiology," Williams & Wilkins (1976) p. 21.) In addition to the RME polysaccharides-arabinogalactan and gum arabic, mannan has also been used according to an embodiment of the invention to deliver steroids to RME receptors on target cells.

netic) iron oxide was prepared as described in Example 6.10.1 of WO 90/01295. An aqueous solution of $FeCl_3$ (15.8 g, 58.5 mole) and $FeCl_2 \cdot 4H_2O$ (6.24 g, 31.6 mmole) was filtered through a 0.22 micron filter to remove large debris. Equal volumes of iron salts and a solution of arabinogalactan from larch wood (60 g, Sigma Chemical Co.) in distilled $H_2O$ (120 mL) were combined at ambient temperature with vigorous stirring. A 30% aqueous ammonium hydroxide solution was then added to the mixture, slowly and dropwise, until the pH reached about 10. The mixture was then heated to a temperature of about 90–100 C. for about 15 minutes. The mixture was allowed to cool and filtered through filters of decreasing porosity of 0.80, 0.45 and 0.22 microns.

Excess arabinogalactan was then removed by ultrafiltration step using a 2 liter hollow fiber unit having a 300 kilodalton cutoff (Amicon, Inc., Danvers, Mass.). The filtered product from the preceding step was loaded into the ultrafiltration unit and washed by the addition of a buffer of 25 mM sodium citrate (pH 8.5). The washing was repeated about 5 times or until a clear eluent was observed. The washed product was then concentrated back to the initial volume of polysaccharide plus metal solutions.

The arabinogalactan coated iron colloid was observed to be cleared by the asialoglycoprotein receptor of hepatocytes and injected iron was identified in the liver, and not in the spleen. This demonstrated that iron was successfully targeted to hepatocytes. For data on the specificity of uptake of iron contrast agents (diagnostic agents) conjugated to arabinogalactan via the asialoglycoprotein receptor, see Table V of Menz et al., PCT WO 90/01295 herein incorporated by reference.

TABLE 3

Therapeutic Agents, RME Polysaccharides and Receptors

| Example | Therapeutic Agent/Disease | RME Polysaccharide | Receptor/Target Cell |
|---|---|---|---|
| 1 | iron oxide/anemia | arabinogalactan | asialoglycoprotein/hepatocyte |
| 2 | iron oxide/anemia | gum arabic | asialoglycoprotein/hepatocyte |
| 3 | folinic acid/chemoprotection | arabinogalactan | asialoglycoprotein/hepatocyte |
| 4 | folinic acid/chemoprotection | gum arabic | asialoglycoprotein/hepatocyte |
| 5 | steroid/anti-inflammatory | arabinogalactan | asialoglycoprotein/hepatocyte |
| 6 | steroid/regulate protein synthesis | gum arabic | asialoglycoprotein/hepatocyte |
| 7 | araAMP/antiviral | gum arabic | asialoglycoprotein/hepatocyte |
| 8 | araAMP/antiviral | arabinogalactan derivative | asialoglycoprotein/hepatocyte |
| 9 | N-acetyl-L-Cysteine/chemoprotection & acetominophen poisoning | gum arabic | asialoglycoprotein/hepatocyte |
| 10 | steroid/anti-inflammatory | mannan | RME receptors/macrophages |

EXAMPLES

Example 1

Arabinogalactan Iron Oxide Colloid

This example describes the preparation of a colloidal iron oxide coated with arabinogalactan, that targets iron to hepatocytes, and has utility in the treatment of iron deficiency. An arabinogalactan coated superparamagnetic (or paramag- The therapeutic potential of the arabinogalactan coated iron oxide for the treatment of iron deficiency anemia was demonstrated when $^{59}Fe$ was used in the synthesis of the coated oxide colloid. The labelled iron was incorporated into normal body iron pools such as iron containing hemoglobin over a period of days. In this way, arabinogalactan coated iron oxide serves as a therapeutic agent when used in the treatment of iron deficiency anemia.

Example 2

Gum Arabic Iron Oxide Colloid

This example describes the preparation of a colloidal iron oxide coated with gum arabic, which was found to target the iron to hepatocytes, and could therefore be used in the treatment of iron deficiency.

The gum arabic used in the following examples was obtained from a Sigma Chemicals, and had a molecular weight of approximately 250,000 daltons as specified by the supplier. The gum arabic was dissolved in water, and filtered through #54 Whatman filter paper, followed by filtration through an 0.8 µM filter to remove particulate weight impurities. The filtered material was ultrafiltered with 5 passes against a 100,000 dalton molecular weight cut off membrane to remove low molecular weight impurities. The retentate was filtered through a 0.2 µm filter to yield a sterile solution, and was then lyophilized.

1.5 ml of 0.93M ferric chloride in 0.1N HCl and 1.5 ml of a 3.14M ferrous chloride solution in 0.1N HCl was added to a 30 ml solution of 50% (w/v) gum arabic solution in deionized water. On adding 40 ml of a 30% (w/v) ammonium hydroxide solution, a black precipitate was formed. The precipitated solution was placed in a boiling water bath for 30 minutes, cooled to room temperature, and passed through a standard 0.22 µm filter. The filtrate was dialyzed against a 0.1 µm hollow fiber filter to remove materials that were unbound to gum arabic covered magnetic particles. The magnetic colloid comprising gum arabic covered magnetic particles formed in this way have a magnetic susceptibility of $45,400 \times 10^6$ c.s.g.

Example 3

Folinic Acid Conjugated to Arabinogalactan

Folinic acid is a vitamin which was coupled to the RME-polysaccharide, arabinogalactan as described below. The drug methotrexate is a folinic acid antagonist and anticancer drug. Methotrexate was attached to RME-polysaccharides and used in drug delivery applications by modifying the folinic acid coupling chemistry shown below.

Folinic acid dihydrate (6.0 mg, 13 µmol) was suspended in $H_2O$ (1 mL). NaOH (0.10N, 7 drops) was added until the white solid folinic acid was almost completely dissolved. Purified arabinogalactan (20,000 daltons, 35.3 mg) was added, followed by 1-(3-dimethylaminopropyl)-3 ethyl-carbo-diimide (51.2 mg, 286 µmol). After stirring for 2.5 hours at room temperature, the reaction mixture was analyzed by HPLC on a Sephadex G-25 column (9.5×300 mm) using an eluent of 0.05% $NaN_3$ (0.33 mL/min). Detection of free and coupled folinic acid was accomplished by using a UV detector, set at 280 nm (for folinic acid, UVmax=283 nm). The chromatogram showed a peak with a retention time of 16.8Êminutes due to folate conjugated to arabinogalactan. Free folinic acid appeared at 35 minutes. These assignment were obtained from chromatographing arabinogalactan and folinic acid. Purified arabinogalactan required a refractive index detector as it does not absorb at 280 nm. Based on UV detection, 37% of the folinic acid was coupled to arabinogalactan. Based on no loss of arabinogalactan and 37% of the folate conjugated, a folate/arabinogalactan ratio of 3:1 was obtained.

Example 4

Attachment of Folinic Acid to Gum Arabic Derivative

Folinic acid is a chemoprotective therapeutic agent whose efficacy can be increased when targeted directly to those cells most in need of chemoprotection. A derivative of gum arabic namely amino gum arabic was used as the RME polysaccharide in this example. The utility of derivatives for providing sites for attachment of therapeutic agents was thereby demonstrated.

Preparation of Amino Gum Arabic.

Ethylene diamine (5 g) was dissolved in 10 ml of DI water. Gum arabic (5 g) was dissolved in 25 ml of DI water. The two solutions were mixed, and the pH was adjusted to between 6 and 6.5 with 6N HCl. 3-Ethylcarbodiimide hydrochloride (EDAC, 7.5 g) was added and stirred until dissolved. Tetraethylethylene Diamine (25 ml) was added to the reaction and the pH was adjusted to 6.5. The mixture was allowed to stir overnight at room temperature. The solution was dialyzed against 4 changes of 40 liters of water. The degree of derivatization was determined using a ninhydrin assay. The results indicate 300 moles of amines per mole of gum arabic, mole/mole.

Conjugation to Folinic Acid.

Folinic acid (25 mg) was dissolved in 1 ml of formamide. To this was added 5 µl of ethylchloroformate and 7.5 µl of TEA. The reaction was allowed to continue for 30 minutes. Amino gum arabic (200 mg) was dissolved in 4 ml of 0.1M phosphate buffer pH 9.0, and the solution was vortexed. The activated folinic acid was added dropwise to the amino gum arabic over several minutes. This reaction was allowed to proceed overnight at room temperature. Any precipitate was re-suspended, and the reaction mixture was fractionated on a PD-10 column (Pharmacia) to separate conjugated from unreacted folinic acid. Phosphate buffer (1 ml) was added to 100 µl each of fraction. The extent of conjugation was determined by measuring the amount of conjugated folinic acid as indicated by its absorbance at 330 nm. The degree of derivatization was determined to be 62.5 folinic acid per molecule of amino gum arabic.

Example 5

Attachment of Steroids to Arabinogalactan-DPTA

Steroids are a class of drugs which can be delivered to cells by attaching them to RME polysaccharides. Example of the chemistry that can be used to couple a variety of steroids to arabinogalactan is given below. The steps include (i) preparation of a polysaccharide conjugate providing carboxyl groups by reaction with DTPA, and (ii) attachment of the steroid through the carboxyl group of the DTPA-polysaccharide.

Preparation of Arabinogalactan-DTPA:

Purified arabinogalactan (23,000 daltons, 0.50 g, 21.7 mol) and diethylene-triaminepentaacetic acid (DTPA) dianhydride (0.102 g, 285 µmol) were dissolved in DMSO (20 mL) at 60° C. After one hour, the clear solution was cooled to room temperature. Upon addition of $H_2O$ (10 mL), a white precipitate formed. The mixture was filtered on an Amicon YM 5 ultrafiltration membrane (5,000 dalton cutoff), and washed with $H_2O$ (4×30 mL). The product remaining on the membrane was dissolved in $H_2O$ (10 mL), frozen and lyophilized. The yield of white powder was 0.44 g. The nominal DTPA/arabinogalactan ration was 13:1, assuming attachment of all DTPA added (nominal formula weight: 28,000 daltons).

Coupling 6-Methylprednisolone to arabinogalactan-DTPA. Arabinogalactan-DTPA (107.5 mg, 3.8 μmole) and 6-methylprednisolone (64.5 mg, 172 μmol) were dissolved in DMSO (15 mL) at 60 C. 1-(3-dimethylaminopropyl)-3-ethylcarbodiimide (259 mg, 1.45 mmol) was added and the reaction mixture allowed to stir at 60 C. for one hour. HPLC analysis (Sephadex G-10 column of 9.5×300 mm with an eluent of 0.05% NAN$_3$, 0.50 mL/min, 280 nm UV detector) of the reaction mixture showed only a single peak at 10.5 minutes retention time corresponding to the mobility of the arabinogalactan-DTPA conjugate. No peak from 6-methylprednisolone at 19.5 minutes was observed, indicating complete attachment (by esterification) of the steroid to the arabinogalactan-DTPA conjugate. After addition of H$_2$O (10ÊmL), the reaction mixture was ultrafiltered using an Amicon YM3 (3,000 dalton cutoff) and washed with H$_2$O (3×30 mL). The filtrate contained unreacted steroid, carbodiimide, traces of DTPA and other low molecular weight materials. HPLC analysis of the filtrate confirmed the absence of free steroid. H$_2$O (10 mL) was added to the retentate and the product lyophilized. The yield of off-white powder was 0.10 g.

Example 6

Attachment of Estradiol to Amino Gum Arabic

An example of the chemistry that can be used to couple a variety of steroids to gum arabic are given below.

Twenty five milligrams of §-Estradiol 3-carboxymethyl ether (Estradiol 3-CME) was dissolved in DMF (1 ml). To this, ethylchloroformate (5 μl) and TEA (7.5 μl) were added. Amino gura arabic (see Example 4, 100 mg) was dissolved in formamide (2 ml), with brief heating. The amino gum arabic was vortexed, and the activated Estradiol 3-CME was added dropwise over several minutes. Conjugated material was separated from unreacted estradiol 3-CME using a PD-10 column that was equilibrated with deionized water. Deionized water (1 ml) was added to 100 μl of each fraction and the degree of derivatization was determined by absorbance at 277 nm and comparison to a standard curve. The results indicate 18.2 estradiol per molecule of amino gum arabic.

Example 7

Attachment of Adenosine Monophosphate (AMP) to Amino Gum Arabic

This example demonstrates the attachment of nucleotides or nucleotide analogs to gum arabic, for targeting the liver. According to the method below, any nucleotide can be coupled to gum arabic including araAMP which has utility as an antiviral agent in the treatment of hepatitis (see Table 1 above).

Amino gum arabic (100 mg) (see Example 4) was dissolved in 1 ml of deionized water. AMP (100 mg) and tetraethylene diamine (500 μl) were added to the amino gum arabic solution. Sodium hydroxide (2N) was added to raise the pH to 6.5. EDAC (100 mg) was added, and the pH adjusted to 6.5. The solution was allowed to react overnight at 37 C. The conjugate was separated from the unreacted AMP using a PD-10 column (Pharmacia) and 100 μl of each fraction was diluted with 1 ml of phosphate buffer. The degree of derivatization was determined by measuring the amount of conjugated AMP as indicated by its absorbance at 260 nm.

Example 8

Attachment of AraAMP to Arabinogalactan Derivative

This example demonstrates the attachment of a therapeutic agent to a hydrolysis product of arabinogalactan. The modification of arabinogalactan in this manner did not affect the ability of the polysaccharide to interact with the RME asialoglycoprotein receptors of the hepatocytes.

Preparation of the Arabinogalactan Hydrolysis Product.

Arabinogalactan (100 g) was dissolved in 37 C. water to give a 20% solution. In a separate container, NaOH (200 g) was dissolved in 37 C. water (5 L). Sodium borohydride 20 g was dissolved in the NaOH solution, and the arabinogalactan solution was then added to this solution. Another 20 g of sodium borohydride was added to the reaction, and the reaction mixture was stirred at 37 C. for 15 min, whereupon the mixture was brought to pH 8.6 by the addition of concentrated cold HCl 4° C. The solution was extensively dialyzed using 3000 molecular weight cut-off dialysis tubing. The dialysate was filtered through an 0.22 micron filter and lyophylized to give the arabinogalactan hydrolysis product as a white crystalline solid. Size exclusion chromatography shows a single component having an average molecular weight of 8 kDa.

Preparation of Carboxymethyl Arabinogalactan (8 kDa) Hydrolysis Product.

Fifty grams of the arabinogalactan 8 kDa hydrolysis product was dissolved in 200 mL of water. To this solution was added one mole of NaOH, followed by bromoacetic acid (70–275 mmols). The reaction was allowed to run for 90 min at 30° C. At the end of the reaction, the solution was neutralized by the addition of 6N HCl. The product was then purified with extensive ultrafiltration using an appropriate filter, then lyophilized. The incorporation of carboxymethyl was 1 milliequivalent per gram.

Attaching the Therapeutic Agent.

The coupling of araAMP to the carboxymethyl 8 kDa hydrolysis product of arabinogalactan was performed in a two step process. To a mixture of ethylene diamine (2.5 mL), adenosine 5-monophosphate (10 g), and 1-hydroxybenzotriazole (HOBt, 3.7Êg) was added 1-ethyl-3-(3-dimethylaminopropyl) carbodiimide (EDC, 15 g) over 3.5 h at 40 C. in 4 portions. The water was removed under vacuum and the product triturated with 50 mL of 2:1 CH$_3$CN/MeOH. The solid was washed with an additional 100 mL of acetonitrile and dried under vacuum at 50 C. The solid was passed through a 2.5 cm×25 cm column containing 100 mL of wet volume Amberlite IR-120 (Na form) ion exchange resin. The fractions containing the product, ethylenediamine-araAMP (en-araAMP, first 250 mL) were combined and the water was removed under vacuum. The product was again triturated with 2:1 acetone/MeOH, and washed with 100 mL of acetone. The product was dried under vacuum for 2 h at 50 C. Yield: 8.2 g.

To attach the en-ARA-AMP to carboxymethyl arabinogalactan, 10 g (1 mEq/g COOH) of carboxymethyl 8 kDa hydrolysis product of arabinogalactan was added to a 350 mL wide mouth jar containing 20 mL of Tetraethylenediamine/HCl buffer (4.0 g, 0.5M, pH 7.5), 1.37 g HOBt and 8.2 g en-araAMP were added. The mixture was heated to 40 C. and then stirred at room temperature overnight. When all the solids had dissolved, 7.6 g EDC was added over 6 h in 3 portions. The crude mixture was diluted 10-fold with water and ultrafiltered through a 3 K filter. After repeated washings with distilled water, the product was lyophilized to a white solid. Yield: 12 g product with 0.50 mmol araAMP/g; approximately 63% of the carboxyl sites on the arabinogalactan hydrolysis product are derivatized.

Example 9

Attachment of N-acetyl-L-Cysteine to Amino Gum Arabic

This example describes the attachment of a chemoprotective agent to a derivative of gum arabic. N-acetyl-L-cysteine is an amino acid that can be used as chemoprotective agent and as an antidote to acetaminophen poisoning of hepatocytes.

N-acetyl-L-cysteine (NAC, 120 mg) was dissolved in 1ÊmlÊof formamide. To this, 12 µl of ethylchloroformate and 20 µl of triethylamine (TEA) was added, and allowed to react for 30 minutes. Amino gum arabic (200 mg) (see Example 4) was dissolved in 4 ml (50 mg/ml) 0.1M phosphate buffer, pH 9.0. This solution was vortexed, and the activated NAC was added dropwise over several minutes. The reaction was allowed to proceed for one hour at room temperature. The solution was passed over a PD-10 column (Pharmacia) to separate conjugated NAC from unreacted NAC. The degree of derivatization was determined using 5,5'-dithio-bis-2-nitrobenzoic acid (DTNB) to assay for sulfhydryl groups. Fifty microliters of each fraction was diluted to 1 ml with 0.1M phosphate buffer (pH 7), and 50 µl of 10 mM DTNB was added. The color generated by reaction of DTNB with sulfhydryl residues was read at 430 nm. The results indicated there were 100 cysteines per molecule of amino gum arabic.

Example 10

Attachment of Therapeutic Agent to Mannan

The attachment of mannan to a therapeutic agent is accomplished following the procedures used in Example 5, and substituting mannan for arabinogalactan.

We claim:

1. A method for targeting a therapeutic agent to a selected population of cells, the cells being characterized by a receptor mediated endocytosis (RME) receptor, comprising (i) forming a complex of the therapeutic agent linked to a polysaccharide molecule selected from the group consisting of gum arabic, mannan, fucoidan, and a hydrolysis product of any of the foregoing; and (ii) allowing the complex to be internalized into the selected population of cells by RME.

2. The method according to claim 1, wherein the polysaccharide is a chemically modified derivative of the polysaccharide, the chemical modification facilitating the formation of the complex between therapeutic agent and the polysaccharide.

3. The method according to claim 1, wherein the polysaccharide is gum arabic.

4. The method according to claim 1, wherein the polysaccharide is mannan.

5. The method according to claim 1, wherein the therapeutic agent is selected from the group consisting of hormones, steroids, nucleic acids, antibodies, vitamins, antiviral agents, enzymes, chemoprotective agents and radioprotecting agents.

6. The method according to claim 1 wherein the therapeutic agent is an antiviral agent.

7. The method according to claim 6, wherein the antiviral agent is araAMP.

8. The method according to claim 1, wherein the therapeutic agent is an antibody.

9. The method according to claim 1, wherein the therapeutic agent is a hormone.

10. The method according to claim 9, wherein the hormone is selected from the group consisting of 6-methylprednisolone, corticosteroid and estrogen.

11. The method according to claim 1, wherein the therapeutic agent is a vitamin.

12. The method according to claim 11, wherein the vitamin is folinic acid.

13. The method according to claim 1, wherein the therapeutic agent is methotrexate.

14. The method according to claim 1, wherein the therapeutic agent is interferon.

15. The method according to claim 1, wherein the therapeutic agent is an iron containing colloid.

16. The method according to claim 1, wherein the RME cell receptor is the asialoglycoprotein receptor.

17. The method according to claim 1, wherein the RME cell receptor is the mannose receptor.

* * * * *